(12) United States Patent
Wilson (10) Patent No.: US 10,831,854 B2
(45) Date of Patent: Nov. 10, 2020

(54) WEB-BASED MEDICAL IMAGE VIEWER WITH WEB DATABASE

(71) Applicant: INTERNATIONAL BUSINESS MACHINES CORPORATION, Armonk, NY (US)

(72) Inventor: Terence Wilson, Newmarket (CA)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 344 days.

(21) Appl. No.: 15/915,806

(22) Filed: Mar. 8, 2018

(65) Prior Publication Data

US 2019/0278869 A1    Sep. 12, 2019

(51) Int. Cl.
| | |
|---|---|
| *G06F 16/00* | (2019.01) |
| *G06F 16/957* | (2019.01) |
| *G16H 30/40* | (2018.01) |
| *G06F 16/51* | (2019.01) |
| *G06F 16/54* | (2019.01) |
| *G06F 16/958* | (2019.01) |

(52) U.S. Cl.
CPC .......... *G06F 16/9574* (2019.01); *G06F 16/51* (2019.01); *G06F 16/54* (2019.01); *G06F 16/9577* (2019.01); *G06F 16/986* (2019.01); *G16H 30/40* (2018.01)

(58) Field of Classification Search
CPC .... G06F 16/9574; G06F 16/986; G06F 16/51; G06F 16/9577; G06F 16/54; G16H 30/40
USPC .......................................................... 707/722
See application file for complete search history.

(56) References Cited

U.S. PATENT DOCUMENTS

| | | | | |
|---|---|---|---|---|
| 7,853,621 | B2* | 12/2010 | Guo ...................... | G06F 16/58 707/803 |
| 2012/0102552 | A1* | 4/2012 | Sammon ................ | G06F 21/31 726/5 |
| 2012/0221535 | A1* | 8/2012 | Dubbels ................ | G06F 19/321 707/694 |
| 2017/0195377 | A1* | 7/2017 | Ahmed ................. | H04L 65/403 |
| 2019/0180861 | A1* | 6/2019 | Reicher ................. | G16H 40/63 |

* cited by examiner

*Primary Examiner* — Monica M Pyo
(74) *Attorney, Agent, or Firm* — Michael Best & Friedrich LLP (57) ABSTRACT

Methods and systems for rending medical images within a web browser application. The web browser application retrieves a worklist and automatically determines an image study from the worklist to be cached. The web browser application retrieves at least one medical image included in the image study. The web browser application creates a web database for storing the at least one medical image within the browser application. When a user selects a medical image for display within the web browser, the web browser application determines whether the medical image is stored in the web database. When the medical image is stored in the web database, the web browser application retrieves the medical image from the web database. When the medical image is not stored in the web database, the web browser application retrieves the medical image from a remote image repository.

17 Claims, 4 Drawing Sheets

WEB-BASED MEDICAL IMAGE VIEWER WITH WEB DATABASE

FIELD

Embodiments described herein relate to a web-based image viewer and, in particular, a web-based image viewer for viewing medical images.

BACKGROUND

Medical images collected as part of medical studies are stored in an image repository. Each medical study may include a large amount of images and each image may include a large amount of data. A medical professional can access and view these medical studies at a remote device. However, based on the network connection and the amount of data being transferred from the image repository, the images may load and display slowly.

SUMMARY

For security and other reasons, web-based applications and services (accessible through a browser application) typically have limited access to other resources of a user device. For example, in some situations, a web-based application or service does not have the ability to access a hard drive or other storage included in the user device. Accordingly, when a web-based application has a large amount of data to load on the user device, the web-based application cannot pre-cache data to improve speed. In some situations, such as in medical image viewing, this delay wastes a radiologist's or medical professional's time.

Accordingly, embodiments described here provide systems and methods for rendering medical images retrieved from a remote image repository within a web browser application executed by an electronic device. For example, one embodiment provides a method that includes retrieving, with an electronic processor executing with the web browser application, a worklist associated with a user identifier and automatically determining, with the electronic processor executing the web browser application, at least one of the plurality of image studies from the worklist to be cached. The method further includes creating, with the electronic processor executing the web browser application, a web database for storing data within the web browser application and retrieving, with the electronic processor executing the web browser application, at least one medical image included in the at least one of the plurality of image studies from a remote image repository over at least one communication network. The method also includes storing, with the electronic processor executing the web browser application, the at least one medical image in the web database and receiving, with the electronic processor executing the web browser application with the web browser, user input selecting a medical image for display within the web browser application. The method further includes determining, with the electronic processor executing the web browser application, whether the medical image selected via the user input is stored in the web database. In response to the medical image selected via the user input being stored in the web database, the method includes retrieving, with the electronic processor executing the web browser application, the medical image from the web database and displaying the medical image on a display device. In response to the medical image selected via the user input not being stored in the web database, the method includes retrieving, with the electronic processor executing the web browser application, the medical image from the remote image repository over the at least one communication network and displaying the medical image on the display device.

Another embodiment provides an electronic device for rendering medical images retrieved from a remote image repository within a web browser application. The electronic device includes a memory storing instructions and an electronic processor coupled to the memory and configured to execute the instructions to implement a web browser application. The web browser application is configured to retrieve a worklist associated with a user identifier and automatically determine at least one of the plurality of image studies from the worklist to be cached. The web browser application is also configured to create a web database for storing data within the web browser application and retrieve at least one medical image included in the at least one of the plurality of image studies from a remote image repository over at least one communication network. The web browser application is further configured to store the at least one medical image in the web database and receive user input selecting a medical image for display within the web browser application. The web browser application is also configured to determine whether the medical image selected via the user input is stored in the web database. In response to the medical image selected via the user input being stored in the web database, the web browser application is configured to retrieve the medical image from the web database and display the medical image on a display device. In response to the medical image selected via the user input not being stored in the web database, the web browser application is configured to retrieve the medical image from the remote image repository over the at least one communication network and displaying the medical image on the display device.

Another embodiment provides a non-transitory computer-readable medium containing instructions that, when executed by an electronic processor, perform a set of functions for rendering medical images retrieved from a remote image repository within a web browser application. The set of functions includes retrieving, with an electronic processor executing with the web browser application, a worklist associated with a user identifier and automatically determining, with the electronic processor executing the web browser application, at least one of the plurality of image studies from the worklist to be cached. The set of functions also includes creating, with the electronic processor executing the web browser application, a web database for storing data within the web browser application and retrieving, with the electronic processor executing the web browser application, at least one medical image included in the at least one of the plurality of image studies from a remote image repository over at least one communication network. The set of functions also includes storing, with the electronic processor executing the web browser application, the at least one medical image in the web database and receiving, with the electronic processor executing the web browser application with the web browser, user input selecting a medical image for display within the web browser application. The set of functions further includes determining, with the electronic processor executing the web browser application, whether the medical image selected via the user input is stored in web database. In response to the medical image selected via the user input being stored in the web database, the set of functions includes retrieving, with the electronic processor executing the web browser application, the medical image from the web database and displaying the medical image on a display device. In response to the medical image selected via the user input not being stored in the web database, the set of functions includes retrieving, with the electronic processor executing the web browser application, the medical image from the remote image repository over the at least one communication network and displaying the medical image on the display device.

Other aspects will become apparent by consideration of the detailed description and accompanying drawings and appendices.

DETAILED DESCRIPTION

One or more embodiments are described and illustrated in the following description and accompanying drawings. These embodiments are not limited to the specific details provided herein and may be modified in various ways. Furthermore, other embodiments may exist that are not described herein. Also, the functionality described herein as being performed by one component may be performed by multiple components in a distributed manner. Likewise, functionality performed by multiple components may be consolidated and performed by a single component. Similarly, a component described as performing particular functionality may also perform additional functionality not described herein. For example, a device or structure that is "configured" in a certain way is configured in at least that way, but may also be configured in ways that are not listed. Furthermore, some embodiments described herein may include one or more electronic processors configured to perform the described functionality by executing instructions stored in non-transitory, computer-readable medium. Similarly, embodiments described herein may be implemented as non-transitory, computer-readable medium storing instructions executable by one or more electronic processors to perform the described functionality. As used in the present application, "non-transitory computer-readable medium" comprises all computer-readable media but does not consist of a transitory, propagating signal. Accordingly, non-transitory computer-readable medium may include, for example, a hard disk, a CD-ROM, an optical storage device, a magnetic storage device, a ROM (Read Only Memory), a RAM (Random Access Memory), register memory, a processor cache, or any combination thereof.

In addition, the phraseology and terminology used herein is for the purpose of description and should not be regarded as limiting. For example, the use of "including," "containing," "comprising," "having," and variations thereof herein is meant to encompass the items listed thereafter and equivalents thereof as well as additional items. The terms "connected" and "coupled" are used broadly and encompass both direct and indirect connecting and coupling. Further, "connected" and "coupled" are not restricted to physical or mechanical connections or couplings and can include electrical connections or couplings, whether direct or indirect. In addition, electronic communications and notifications may be performed using wired connections, wireless connections, or a combination thereof and may be transmitted directly or through one or more intermediary devices over various types of networks, communication channels, and connections. Moreover, relational terms such as first and second, top and bottom, and the like may be used herein solely to distinguish one entity or action from another entity or action without necessarily requiring or implying any actual such relationship or order between such entities or actions.

Figure 1:
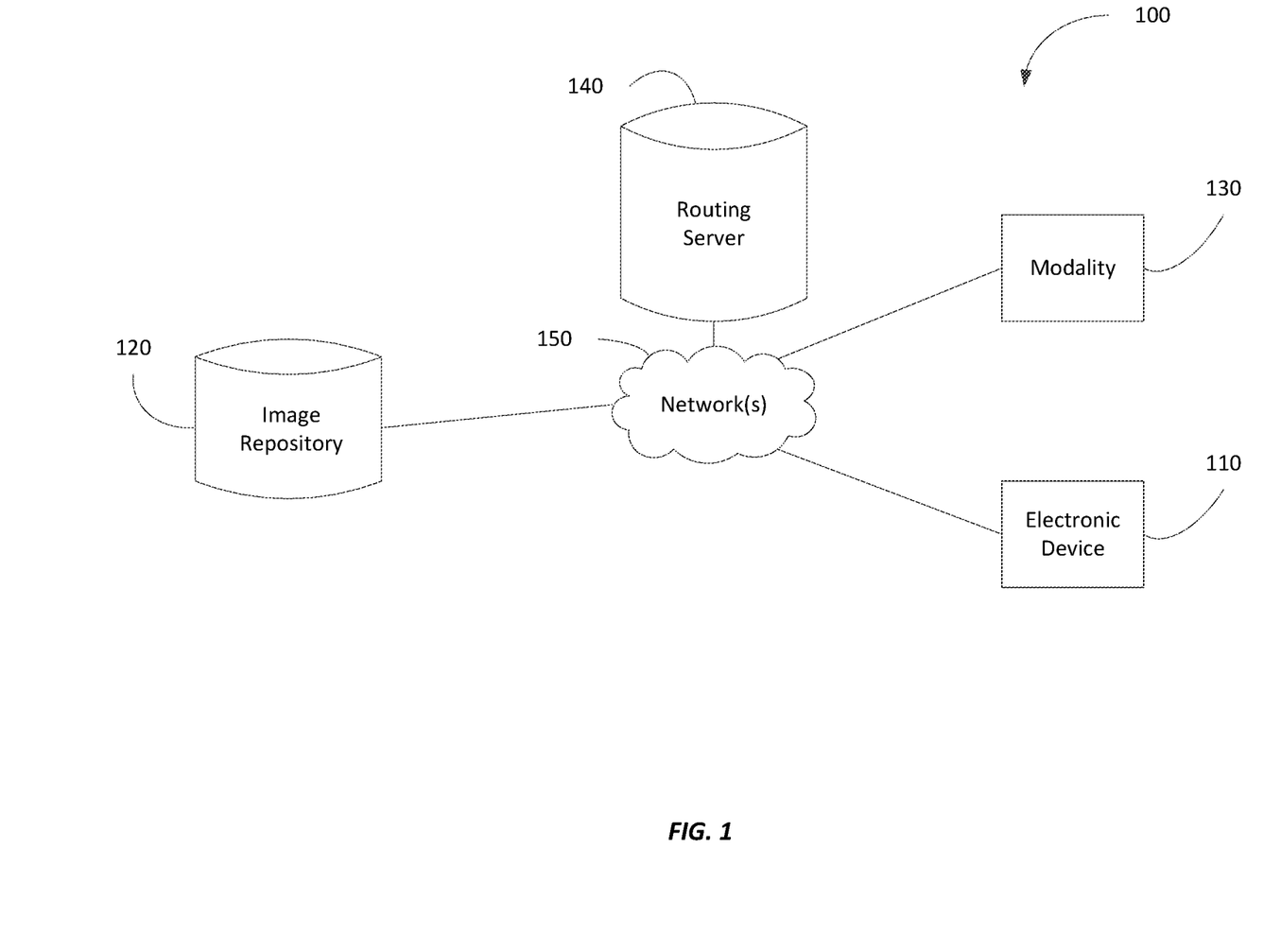
FIG. 1 schematically illustrates a system for rendering medical images on an electronic device received from a remote image repository.

FIG. 1 illustrates a system 100 for rendering medical images on an electronic computing device 110 from a remote image repository 120. The electronic device 110 can include a device associated with a recipient of a medical study, such as a radiologist or a physician ordering the imaging procedure. For example, the electronic device 110 may be a desktop computer, a terminal or workstation, a laptop computer, a tablet computer, a smart watch or other wearable, a smart telephone, and the like. The medical images are generally generated by a modality 130, such as an X-Ray imaging system, a magnetic resonance imaging (MRI) system, a computed axial tomography (CAT) system. The medical images generated by the modality 130 are routed by a central hub or routing server 140 over one or more wired or wireless networks 150 (e.g., the Internet, a clinical messaging network, a local area network, etc.) to be stored on the image repository 120. In some embodiments, the system 100 includes additional components, such as multiple electronic devices 110, multiple image repositories 120, multiple routing servers 140, or the like. Also, in some embodiments, the routing server 140 may include an image repository.

The routing server 140 may be, for example, a picture archiving and communication system (PACS) server that serves as a gateway to the image repository 120. The routing server 140, the image repository, or both may be associated with a particular type or brand of modality 130 or may be configured to handle images generated by a variety of types and brands of modalities. Also in some embodiments, the image repository 120 can be included in the routing server 140. In some embodiments, the routing server 140 also includes a web server that responds to requests received from one or more web browser applications. However, in other embodiments, a web server separate from the routing server 140 services these requests by acting as an intermediary device between the web browser applications and the routing server 140.

Figure 2:
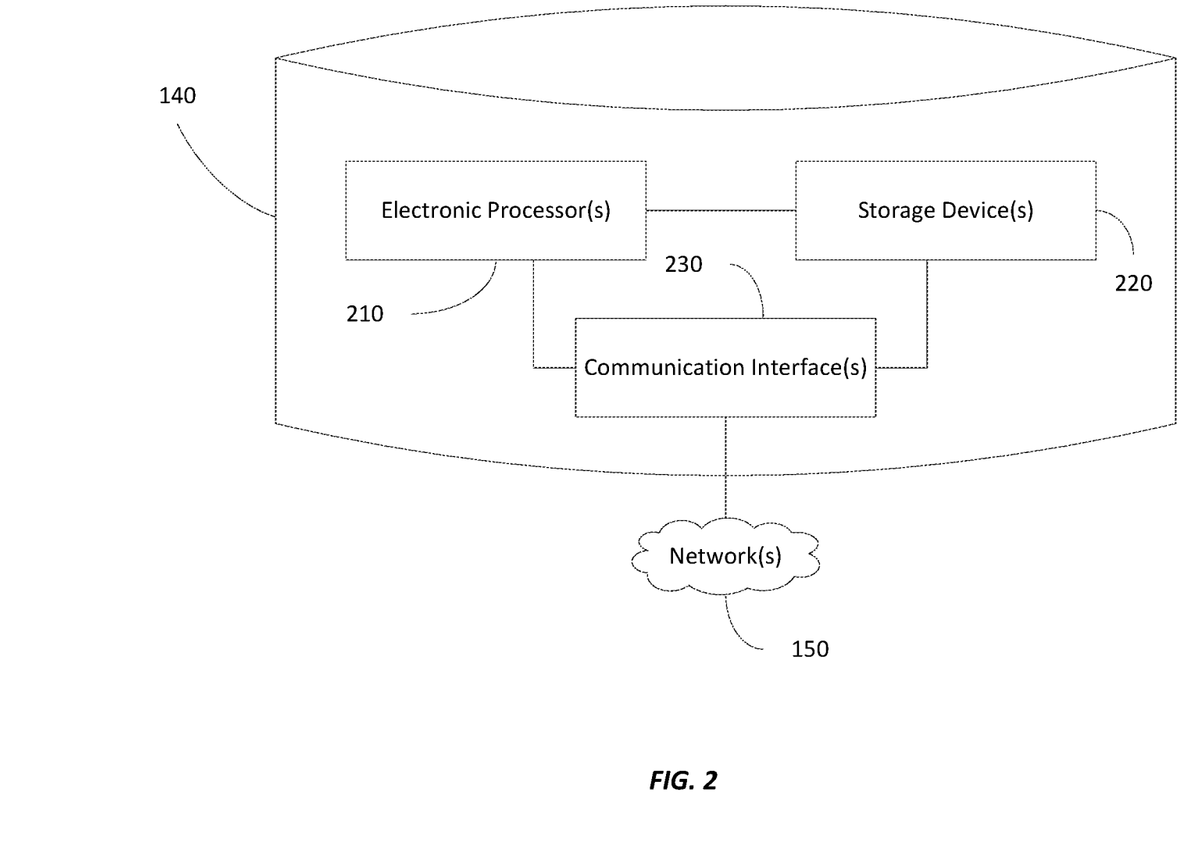
FIG. 2 schematically illustrates a routing server included in the system of FIG. 1.

As illustrated in FIG. 2, the routing server 140 includes one or more electronic processors 210, one or more computer-readable memory or storage devices 220, and one or more communication interfaces 230. The storage devices 220 can include non-transitory memory, such as random access memory and/or read-only memory. The electronic processors 210 can include a microprocessor or other electronic device configured to execute instructions stored in the storage devices 220. The storage devices 220 can also store data used with and generated by execution of the instructions. The communication interfaces 230 allow the routing server 140 to communicate with external devices over the networks 150. The routing server 140 can use the networks 150 to communicate with the electronic device 110, the image repository 120, and the modality 130 and, in some embodiments, uses different networks 150 to communicate with each device. However, in some embodiments, the routing server 140 can be configured to have a dedicated interface or connection one or more devices, such as the image repository 120.

It should be understood that in some embodiments, the server 140 includes additional components than those illustrated in FIG. 2. It should also be understood that, in some embodiments, the functionality provided by the server 140 as described herein can be distributed among multiple servers, such as servers included in a cloud service or environment. In addition, it should be understood that although only a single electronic device 110 and a single modality 130 are illustrated in FIG. 1, the routing server 140 can be configured to communicate with multiple different electronic devices 110 and modalities 130.

Figure 3:
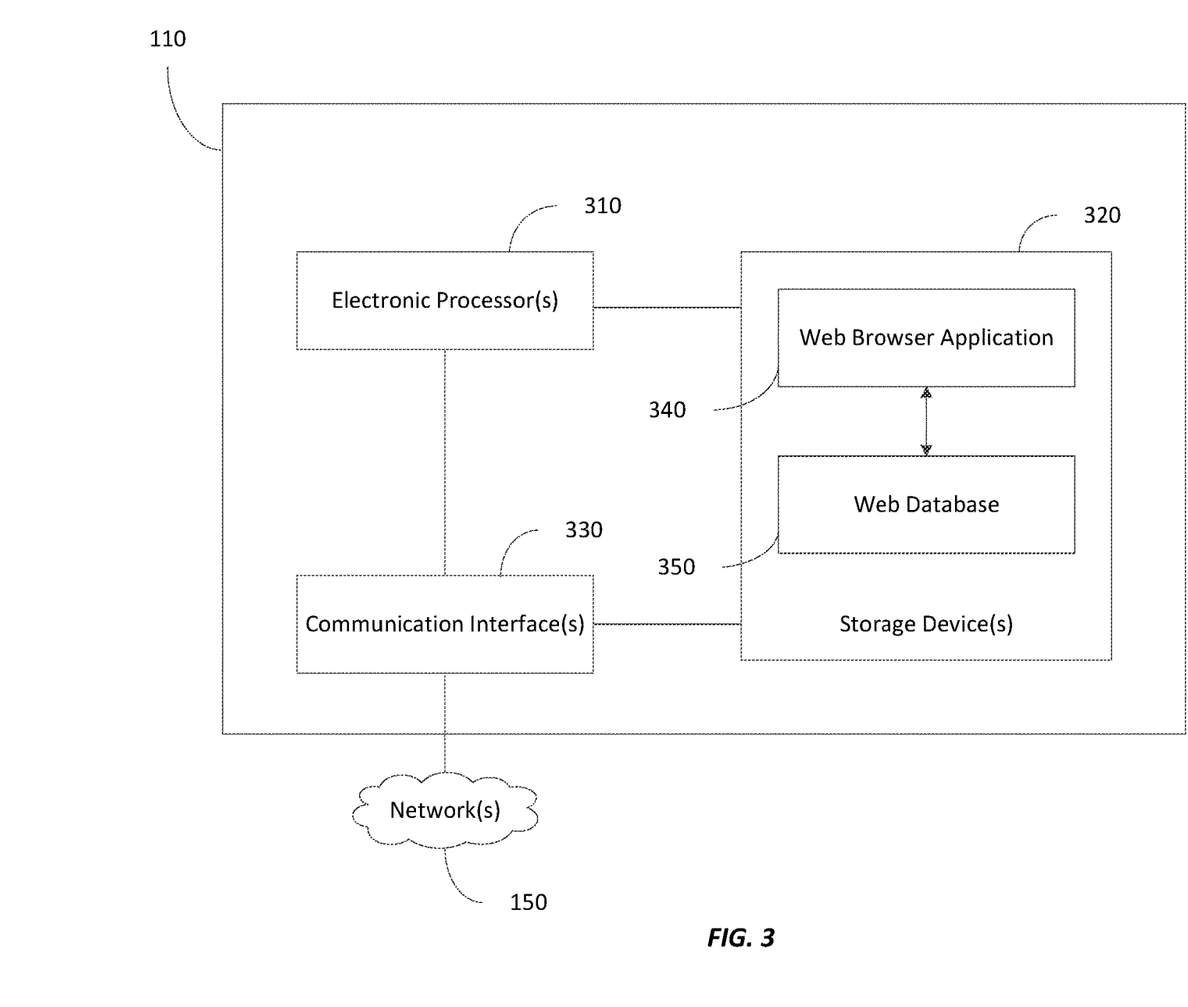
FIG. 3 schematically illustrates the electronic device included in the system of FIG. 1.

As illustrated in FIG. 3, the electronic device 110 includes some similar components as the routing server 104. In particular, the electronic device 110 includes one or more electronic processors 310, one or more computer-readable storage devices 320, and one or more communication interfaces 330. The storage devices 320 can include non-transitory memory, such as random access memory and/or read-only memory. The electronic processors 310 can include a microprocessor or other electronic device configured to execute instructions stored in the storage devices 320. The storage devices 320 can also store data used with and generated by execution of the instructions. The communication interfaces 330 allow the electronic device 110 to communicate with external devices over the networks 150. The electronic device 110 can use the networks 150 and a web server to communicate with the routing server 140 and the image repository 120 and, in some embodiments, uses different networks 150 to communicate with each device. Although not illustrated in FIG. 3, the electronic device 110 may also include one or more human machine interfaces for receiving input from a user, providing output to a user, or a combination thereof. For example, the electronic device 110 may also include a keyboard, a mouse, an LCD display, an LED display, a touch screen display, or a combination thereof. It should be understood that in some embodiments, the electronic device 110 includes additional components than those illustrated in FIG. 3 or components in different configurations than those illustrated in FIG. 3.

The storage devices 320 included in the electronic device 110 stores, among other things, a web browser application 340 and a web database 350 for storing data within the web browser application 340. The web browser application 340 is, for example, Mozilla Firefox, Google Chrome, Internet Explorer, and the like. The web browser application 340 receives a Uniform Resource Locater (URL) that directs the web browser application 340 to a web server (for example, the routing server 140 or a separate intermediary web server as described above). The web browser application 340 retrieves and executes, for example, a Hypertext Markup Language (HTML) code from the web server. The web browser application 340 may create one or more web databases 350 based on executing the HTML code as further described below. In particular, the web browser application 340 may use capabilities present in HTML 5 to create the web databases 350 (IndexedDB) to improve performance. For example, IndexDB is an application programming interface (API) which allows HTLM5 web applications to store (persistently) data inside a user's browser via a web database. Accordingly, the web databases 350 can be used to store certain files and data retrieved from the web server, such as images. Accordingly, the web databases 350 are a transactional databases embedded in the web browser application. As described in further detail below, the web databases 350 may be organized around the concept of collections of objects (JSON objects), wherein each object is identified with a key generated during insert and an indexing system optimizes access to the stored objects. Accordingly, as compared to cookies or other options for client-side storage, a web database, as described herein, provides database-like usability (query abilities and online and offline availability), which allows a web database to handle large amounts of data. Furthermore, cookies result in additional traffic and may be limited in space. In addition, many users block cookies, which limits the usability of this client-side storage option.

A user may access images in the image repository 120 by entering a URL associated with the server 140 in the web browser application 340 executed by the electronic device 110. In some embodiments, the pages or user interfaces (UIs) accessible via the URL (as executed and rendered within the web browser application 340) may prompt the user to enter the user's login credentials, a user identifier associated with the user, or other authenticating information. After any required authentication is complete, the user can access and view one or more images stored in the image repository 120. In some embodiments, the user may submit a request for specific images stored in the image repository. In addition or alternatively, images may be automatically downloaded and cached in the web database 350 for use in responding to subsequent user requests for particular images. It should be understood that functionality described hereafter as being performed by the web browser application 340 may be performed by the application 340 as stored and executed on the electronic device 110 through the execution of code (HTML code) received from the routing server 140 (or a separate web server).

Figure 4:
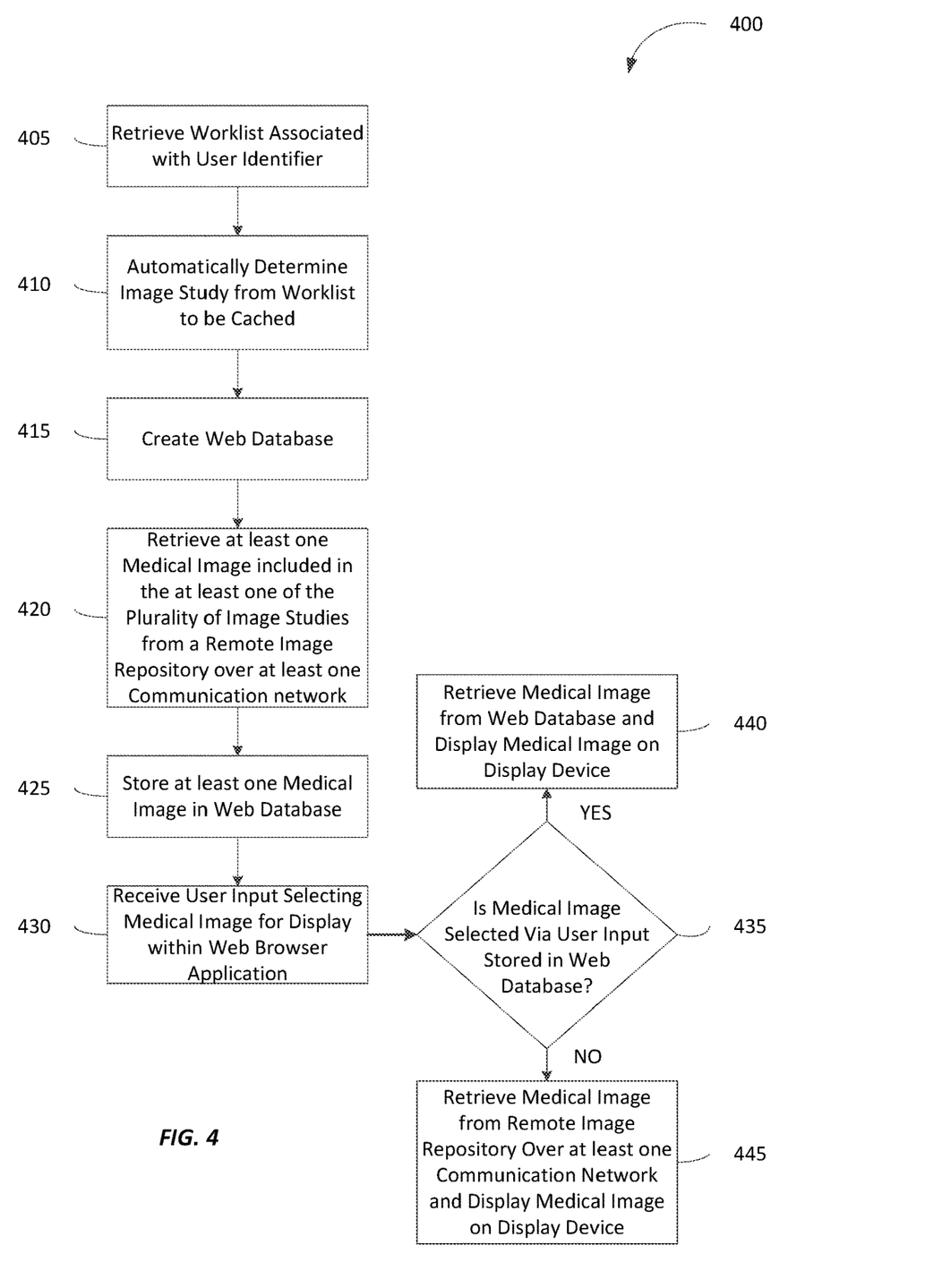
FIG. 4 is a flowchart illustrating a method for rendering images on an electronic device performed by the system of FIG. 1.

For example, FIG. 4 is a flowchart illustrating a method 400 for rendering medical images, stored in the remote image repository 120, on the electronic device 110 from the remote image repository 120. The method 400 is described as being performed by the electronic device 110 (in particular, the electronic processors 310 executing instructions, including the web browser application 340).

As illustrated in FIG. 4, the method 400 includes retrieving a worklist associated with a user identifier (such as associated with a user identifier received or determined as part of receiving authenticating information) (at block 405). A worklist is an organizational structure that lists image studies a user is interested in reviewing and analyzing. For example, a physician's worklist may include image studies ordered by the physician for his or her patients, and a radiologist's worklist may include image studies needing reading. Worklists may include image studies conducted for one or more patients. Accordingly, the worklist includes a plurality of image studies and each of the plurality of image studies includes a plurality of medical images. The worklist for a user may be stored on the electronic device 110 (the storage devices 320), the routing server 140, a separate server, or a combination thereof. For example, the web browser application 340 may request the worklist associated with the user by providing a user identifier to the routing server 140. The server 140 may determine the worklist associated with the user identifier, such as by using a look-up table, and send the worklist (or a portion thereof, such as identifiers for a predetermined number of image studies included in the worklist) to the electronic device 110 over the networks 150. The data regarding the worklist (the worklist data) received by the electronic device 110 may include unique identifiers of the image studies, unique identifiers of medical images included in image studies, or a combination thereof. The web browser application 340 may display the worklist including, for example, names and thumbnails of image studies to receive a selection from the user.

As illustrated in FIG. 4, the method 400 also includes automatically determining at least one of the plurality of image studies from the worklist to be cached (at block 410). Several techniques may be used to identify which image study needs to be cached. In some embodiments, a subset of the image studies is cached. In other embodiments, all of the image studies in the worklist are cached (for example, sequentially). Alternatively or in addition, the most recent image study may be cached. Alternatively or in addition, the identification of the image study to be cached may depend on a browsing history associated with the user, a role of the user, previous user input, a current date or time, a schedule of the user (how long the user has been working, is scheduled to work, is next scheduled to work, and the like), past performance of the user (how quickly the user completed other image studies), and the like.

The method 400 further includes creating a web database 350 (at block 415) in the local storage devices 320 of the electronic device 110. The web database 350 is embedded within the web browser application. In some embodiments, the storage devices 230 are segmented to allow for use with several applications of the electronic device 110. The web browser application 340 may select or determine one or more segments of the storage devices 320 to assign the web database 350. The web database 350 may be configured to be an object storage to store the images and files as objects. The web database 350 may also implement a random storage technique to store images and files. In particular, rather than being sequential, the location of each image or file may be associated with a unique key. That is, each image or file is indexed to a key. Accordingly, when a key is inputted to the web database 350, the web database 350 returns the location of the image or file associated with the key. In some embodiments, the web database 350 may be created for use with all webpages and web applications that may be accessed via the web browser application 340. In other embodiments, the web database 350 may be specifically created for the web-based image viewer associated with the routing server 140. In some embodiments, the web browser application 340 may open a previously-created web database 350 at block 415 when such a database already exists.

The method 400 also includes retrieving at least one medical image included in the at least one of the plurality of image studies from the remote image repository 120 over at least one communication network 150 (at block 420). The web browser application 340 may request one or more medical images associated with the image study by providing an image identifier to the server 140 over the networks 150. The server 140 receives the image identifier, retrieves the one or more medical images associated with the image identifiers from the image repository 120, and transmits the medical image to the electronic device 110 over the networks 150. In some embodiments, rather than retrieving the medical image from the image repository 120, the server 140 may instruct the image repository 120 to transmit the medical image directly to the electronic device 110. The web browser application 340 may retrieve the medical image as Binary Large Objects (BLOBs). BLOBs are packets of data that may include partial or complete data of a medical image. In some embodiments, the medical image may be retrieved in other formats.

The method 400 further includes storing the at least one medical image in the web database 350 (at block 425). The web browser application 340 initiates a transaction with the web database 350 for each medical image and stores the medical image in the web database 350 during each transaction. In some embodiments, the web browser application 340 assigns a key to a location where the medical images is stored. The web browser application 340 associates each key with a link or locator for the particular medical image. As described below, the link or locator for the medical image is used to call or retrieve the medical image from the web database 350 when the user selects (e.g., by clicking) the medical image on a user interface displayed via the web browser application 340. The method 400 may repeat blocks 420 and 425 for each medical image in the image study to store the medical images in the web database 350.

The method 400 further includes receiving user input selecting of a medical image for display within the web browser application 340 (at block 430). The user may select the medical image to be viewed on a user interface displayed via the web browser application 340 (such as within displayed worklist data). The web browser application 340 may receive the unique key associated with the selected medical image in response to such a selection.

After receiving the selection, the method 400 includes determining whether the medical image selected via the user input is stored in the web database 350 (at block 435). The web browser application 350 may determine whether the medical image is stored in the web database 350 based on the presence or absence of a unique key associated with the selection. The web browser application 340 determines that the medical image is stored in the web database when the unique key associated with the selected medical image is received in response to the selection by the user. The web browser application 340 determines that the medical image is not stored in the web database 350 when an identifier associated with the medical image is received instead of the unique key.

In response to the medical image selected via the user input being stored in the web database 350, the method 400 includes retrieving the medical image from the web database 350 and displaying the medical image on a display device of the electronic device 110 (at block 440). The web browser application 340 may initiate another transaction with the web database 350 and retrieve the medical image from the web database 350 using the transaction. In response to the medical image selected via the user input not being stored in the web database, the method 400 includes retrieving the medical image from the image repository 120 over the at least one communication network 150 and displays the medical image on the display device of the electronic device 110 (at block 445). The display device is a human machine interface that illustrates a user interface of the web browser application 340.

Thus, by implementing a web database, a web browser application is able to cache medical images viewed through a web-based viewing application, which improves performance. In particular, by accessing a worklist of a user of the web-based viewing application, the web browser application is able to automatically pre-download or cache medical images that the user likely will request access to in the future to further improve viewing performance.

Various features and advantages of the invention are set forth in the following claims.

What is claimed is:

1. A method for rendering medical images within a web browser application, the method comprising:

retrieving, with an electronic processor executing with the web browser application, a worklist associated with a user identifier, the worklist including a plurality of image studies;

automatically determining, with the electronic processor executing the web browser application, at least one of the plurality of image studies from the worklist to be cached;

creating, with the electronic processor executing the web browser application, a web database for storing data within the web browser application, the indexed database embedded within the web browser application;

retrieving, with the electronic processor executing the web browser application, at least one medical image included in the at least one of the plurality of image studies from a remote image repository over at least one communication network;

storing, with the electronic processor executing the web browser application, the at least one medical image in the web database;

receiving, with the electronic processor executing the web browser application with the web browser, user input selecting a medical image for display within the web browser application;

determining, with the electronic processor executing the web browser application, whether the medical image selected via the user input is stored in web database;

in response to the medical image selected via the user input being stored in the web database, retrieving, with the electronic processor executing the web browser application, the medical image from the web database and displaying the medical image on a display device; and in response to the medical image selected via the user input not being stored in the web database, retrieving, with the electronic processor executing the web browser application, the medical image from the remote image repository over the at least one communication network and displaying the medical image on the display device, wherein automatically determining the at least one of the plurality of image studies includes selecting the at least one of the plurality of image studies based on at least one selected from a group consisting of a user, a role of the user, previous input received from the user, a current date or time, a schedule of the user, and past performance of the user.

2. The method of claim 1, further comprising retrieving the user identifier from a user via the web browser application.

3. The method of claim 1, wherein retrieving the worklist includes retrieving the worklist from at least one selected from a group consisting of the remote image repository, a routing server associated with the remote image repository, a storage device of an electronic device including the electronic processor, or a combination thereof.

4. The method of claim 1, wherein automatically determining the at least one of the plurality of image studies includes selecting a subset of the plurality of image studies included in the worklist.

5. The method of claim 1, wherein automatically determining the at least one of the plurality of image studies includes selecting the plurality of image studies.

6. The method of claim 1, wherein automatically determining the at least one of the plurality of image studies includes selecting a most recent image study of the plurality of image studies.

7. The method of claim 1, wherein storing the at least one medical image in the web database includes storing each of a plurality of medical images included in the at least one of the plurality of image studies in the web database sequentially.

8. The method of claim 7, further comprising assigning a key to each of the plurality of medical images stored in the web database and wherein retrieving the medical image from the web database includes retrieving the medical image from the web database using the key assigned to one of the plurality of medical images.

9. The method of claim 1, wherein creating the web database includes opening a previously-created web database.

10. The method of claim 1, wherein retrieving the medical image from the remote image repository includes sending an image identifier associated with the medical image to a routing server associated with the image repository.

11. A non-transitory computer-readable medium containing instructions that, when executed by an electronic processor, perform a set of functions, the set of functions comprising:

retrieving, with an electronic processor executing with the web browser application, a worklist associated with a user identifier, the worklist including a plurality of image studies;

automatically determining, with the electronic processor executing the web browser application, at least one of the plurality of image studies from the worklist to be cached;

creating, with the electronic processor executing the web browser application, a web database for storing data within the web browser application, the web database embedded within the web browser application;

retrieving, with the electronic processor executing the web browser application, at least one medical image included in the at least one of the plurality of image studies from a remote image repository over at least one communication network;

storing, with the electronic processor executing the web browser application, the at least one medical image in the web database;

receiving, with the electronic processor executing the web browser application with the web browser, user input selecting a medical image for display within the web browser application;

determining, with the electronic processor executing the web browser application, whether the medical image selected via the user input is stored in web database;

in response to the medical image selected via the user input being stored in the web database, retrieving, with the electronic processor executing the web browser application, the medical image from the web database and displaying the medical image on a display device; and in response to the medical image selected via the user input not being stored in the web database, retrieving, with the electronic processor executing the web browser application, the medical image from the remote image repository over the at least one communication network and displaying the medical image on the display device, wherein automatically determining the at least one of the plurality of image studies includes selecting the at least one of the plurality of image studies based on at least one selected from a group consisting of a user, a role of the user, previous input received from the user, a current date or time, a schedule of the user, and past performance of the user.

12. The non-transitory computer-readable medium of claim 11, wherein retrieving the worklist includes retrieving the worklist from at least one selected from a group consisting of the remote image repository, a routing server associated with the remote image repository, a storage device of an electronic device including the electronic processor, or a combination thereof.

13. The non-transitory computer-readable medium of claim 11, wherein storing the at least one medical image in the web database includes storing each of a plurality of medical images included in the at least one of the plurality of image studies in the web database sequentially.

14. The non-transitory computer-readable medium of claim 13, the set of functions further comprising:
assigning a key to each of the plurality of medical images stored in the web database and wherein retrieving the medical image from the web database includes retrieving the medical image from the web database using the key assigned to one of the plurality of medical images.

15. An electronic device for rendering medical images from a remote image repository, the electronic device comprising:
a memory storing instructions; and
an electronic processor coupled to the memory and configured to execute the instructions to implement a web browser application, the web browser application configured to:
retrieve a worklist associated with a user identifier, the worklist including a plurality of image studies;
automatically determine at least one of the plurality of image studies from the worklist to be cached;
create a web database, the web database embedded within the web browser application;
retrieve at least one medical image included in the at least one of the plurality of image studies from a remote image repository over at least one communication network;
store the at least one medical image in the web database;
receive user input selecting a medical image for display within the web browser application;
determine whether the medical image selected via the user input is stored in web database;
in response to the medical image selected via the user input being stored in the web database, retrieve the medical image from the web database and displaying the medical image on a display device; and
in response to the medical image selected via the user input not being stored in the web database, retrieve the medical image from the remote image repository over the at least one communication network and displaying the medical image on the display device,
wherein automatically determining the at least one of the plurality of image studies includes selecting the at least one of the plurality of image studies based on at least one selected from a group consisting of a user, a role of the user, previous input received from the user, a current date or time, a schedule of the user, and past performance of the user.

16. The electronic device of claim 15, wherein storing the at least one medical image in the web database includes storing each of a plurality of medical images included in the at least one of the plurality of image studies in the web database sequentially.

17. The electronic device of claim 16, wherein the web browser application is further configured to:
assign a key to each of the plurality of medical images stored in the web database and wherein retrieving the medical image from the web database includes retrieving the medical image from the web database using the key assigned to one of the plurality of medical images.

* * * * *